United States Patent [19]

Kato

[11] Patent Number: 4,874,944
[45] Date of Patent: Oct. 17, 1989

[54] MASS SPECTROMETER
[75] Inventor: Yoshiaki Kato, Mito, Japan
[73] Assignee: Hitachi, Ltd., Tokyo, Japan
[21] Appl. No.: 149,223
[22] PCT Filed: Jun. 26, 1987
[86] PCT No.: PCT/JP87/00434
  § 371 Date: Jan. 13, 1988
  § 102(e) Date: Jan. 13, 1988
[87] PCT Pub. No.: WO87/01452
  PCT Pub. Date: Mar. 12, 1987
[30] Foreign Application Priority Data
  Jul. 4, 1986 [JP] Japan ................. 61-156056
[51] Int. Cl.$^4$ ............................................. B01D 59/44
[52] U.S. Cl. ................................ 250/288; 250/299; 250/300
[58] Field of Search ............... 250/281, 282, 283, 298, 250/299, 300, 442.1, 252.1, 288 A

[56] References Cited
U.S. PATENT DOCUMENTS 2,837,653  6/1958  Craig et al. ..................... 250/300
3,288,994  11/1966 Omura et al. ................... 250/299
3,896,661  7/1975  Parkhurst et al. ............. 250/288 A
4,259,572  3/1981  Brunner et al. ................ 250/288 A

FOREIGN PATENT DOCUMENTS 2143673  2/1985  United Kingdom ........... 250/288 A

OTHER PUBLICATIONS

"Use of a Mass Spectrometer as a Detulor and Analzer for Effluents Energizing from High Temperature Gas Liquid Chromatography Columsn", Ryhage, *Anal. Chem.*, vol. 36, No. 4, Apr. 1964, pp. 759–764, 250–288 A.

Primary Examiner—Bruce C. Anderson
Attorney, Agent, or Firm—Antonelli, Terry & Wands

[57] ABSTRACT

An apparatus for mass-analyzing ions that are generated by bombarding sample components supported by a target by a primary beam. The mass spectrum data thus obtained is preferably as correct as possible. To satisfy this requirement, mass number sweeping is started after the quantity of ions generated from the sample components becomes gets stabilized.

8 Claims, 2 Drawing Sheets

MASS SPECTROMETER

TECHNICAL FIELD

This invention relates to a mass spectrometer which will be suitable for direct mass analysis of sample components developed and held by a target such as a thin layer chromatography plate.

BACKGROUND ART

In order to obtain mass spectra of sample components developed and held on a TLC plate (Thin Layer Chromatography plate), a technique has been known which scrapes off the sample components, and after extracting and purifying them, introduces them into a mass spectrometer.

However, such a method of obtaining mass spectra involves the problems in that not only the method is extremely troublesome to practice and time consuming, information on the mixture state is completely lost if the sample components developed are a mixture.

Therefore, proposals have been made to introduce the TLC plate into a mass spectrometer and to obtain the mass spectra by SIMS (Secondary Ion Mass Spectrometry) or FAB (Fast Atom Bomberdment). In accordance with these proposals, while the TLC plate is moving in the direction of development of the sample components developed and held on the TLC plate, the TLC plate is bombarded by an accelerated and converged ion beam or by a fast speed atomic beam and ions obtained from the sample components are subjected to mass-analysis in order to obtain the mass spectra of the sample components. According to this method, the mass spectra can be obtained one after another and moreover, mass chromatogram can be obtained immediately by putting data in order and tracing the current value of a specific ion or the current value of all the ions.

When the sample components are bombarded by the ion beam or the fast speed atomic beam, the bombarded portion is locally sputtered so that occurrence of ions decreases. Therefore, a matrix such as glycerol is coated generally on the surface of TLC prior to the analysis in order that the sample components around the low ion portion migrate to it and the drop of the ion occurrence can be prevented.

Incidentally, the SIMS (or FAB) analysis method of the sample components on the TLC plate is described, for example, in "Journal of Biochemistry", Vol. 98, 1985, pp. 265–268.

As a result of experiments and studies, the inventor of the present invention has found out the following.

(1) Immediately after the primary beam bombardment, a phenomenon wherein large amounts of ions occur from the matrix surface (FIG. 1-II) or a phenomenon wherein ions hardly occur, (FIG. 1-II) on the contrary, takes place.

(2) If the primary beam bombardment is continued, the occurrence of ions changes drastically and about one or two minutes later, gets stabilized (FIGS. 1-I and 1-II). Though this time T till stabilization depends on the matrix to be added or the like, it hardly exceeds several minutes.

(3) It is assumed that the ion occurrence gets stabilized when electrical and physico-chemical equilibrium is attained.

(4) When the mass spectra are obtained by moving the TLC plate, a new surface is always bombarded by the primary beam. Accordingly, in this case, the mass spectra and mass chromatogram contain great changes and cannot be correct from the facts described above. In other words, FIG. 2-I shows the expected mass chromatogram while the mass chromatogram obtained in practice contains a great change as shown in FIG. 2-II and is not accurate.

DISCLOSURE OF INVENTION

It is therefore an object of the present invention to provide a mass spectrometer which will be suitable for obtaining stable mass spectra in view of the facts described above.

In accordance with the present invention, the movement of the target is controlled so that the target is stopped when the sample components supported by the target reach the primary beam bombardment position, and mass number sweeping is started after the passage of a predetermined period till the ion quantity from the sample components gets substantially stabilized from the time at which the target is stopped.

Movement control of the target is effected so that the target stops when the sample components reach the primary beam bombardment position and mass number sweeping is started after the passage of a predetermined period of time from the stop of the target till the ion quantity from the sample components gets substantially stabilized. Therefore, incorrectness of the resulting mass spectra can be prevented and correct mass spectra can be obtained.

BEST MODE FOR CARRYING OUT THE INVENTION

Figure 1:
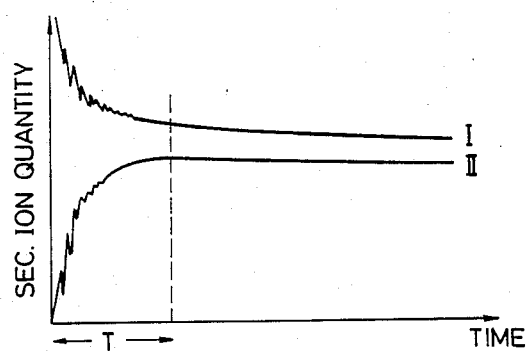
FIG. 1 shows a secondary ion quantity after primary beam bombardment by an SIMS (FAB) method.
Figure 2:
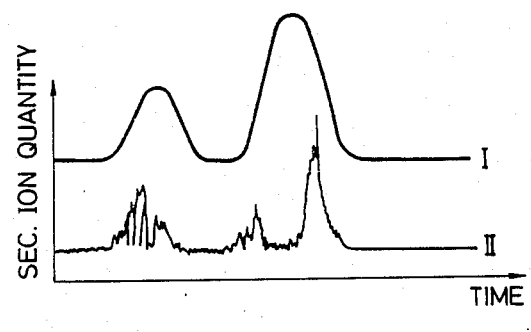
FIG. 2 shows the mass chromatogram obtained by a TLC/SIMS (FAB) method.
Figure 3:
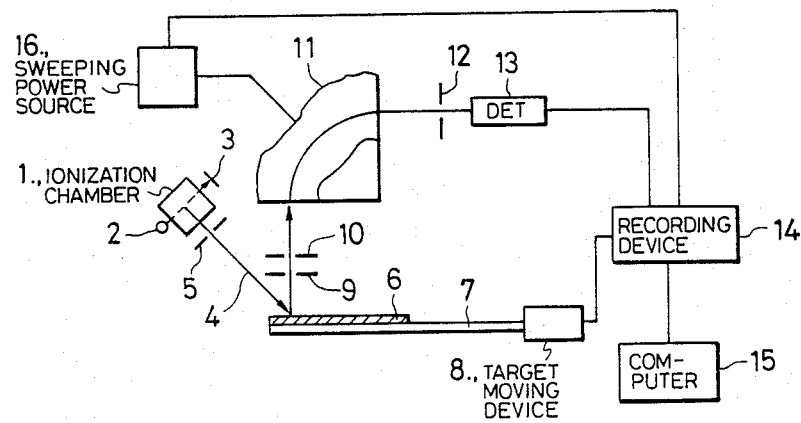
FIG. 3 is a conceptual view of a mass spectrometer in accordance with one embodiment of the present invention.

Referring to FIG. 3, an inert gas such as xenon gas is introduced into an ionization chamber 1 and is ionized by bombardment of electrons that are emitted from a filament 2 toward a collector 3. The ions which are generated are accelerated by an acceleration voltage of about 8 to 10 kV that is applied to the ionization chamber 1, and are emitted as an ion beam 4 out of the ionization chamber 1. The ion beam which serves as a primary beam is focused by a lens electrode 5 on a target 6.

The target 6 consists of a TCL plate. Namely, the target 6 includes a substrate such as aluminum and an adsorption layer such as silica gel formed on the surface thereof. Sample components developed and separated by TCL are adsorbed and supported by the adsorption layer, and a matrix such as glycerol is coated onto the surface of the adsorption layer.

The target 6 is held by a target holder 7, which is supported by a target moving device 8. Assuming that a certain component of the sample components on the target 6 is moved by the target moving device 8, then the sample component is sputtered by the ion beam 4 and secondary ions are generated from it. The acceleration voltage of about 3 kV is applied to the target 6 so that the energy of ion beam 4 that impinges against the target 6 is from 5 to 7 keV and the energy which accelerates the secondary ions is 3 keV.

The accelerated secondary ions pass through a lens slit 9 and a source slit 10 and are separated depending on their mass number by a magnetic field generated by a magnet 11. In other words, mass-dispersion is effected. Among the ions that are mass-dispersed, the ions of a particular mass number that pass through a collector slit 12 are detected by a detector 13. A computer 14 controls a magnetic field sweeping power source 16 to sweep the magnetic field. Accordingly, the ions having various mass numbers are sequentially detected by the detector 13 and mass number sweeping is effected.

Signals from the detector 13 are all stored in the computer 14, which produces a chromatogram signal by total ions, a chromatogram signal by ions of a particular mass number and a mass spectrum signal, on the basis of the data stored therein. The output signals from the computer 15 are recorded in a recording device 15.

Figure 4:
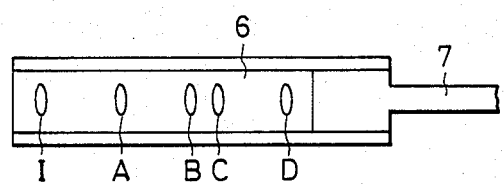
FIG. 4 is a plan view of the target shown in FIG. 3.

In FIG. 4, symbol I denotes a position where a mixture sample will be added and symbols A to D denote sample components that are developed and separated by means of TLC. Usually, the portions I and A to D are colored so that they can be distinguished form other portions with naked eyes. When the portion I is regarded as a reference position, therefore, the positions A to D can be easily measured using a rule. When the portion I is regarded as a reference position, the measured positions A to D and sizes of the sample components A to D in a direction in which the TLC plate 6 moves are stored in the computer 14.

The target moving device 8 moves and controls the target 6 in such a manner as to stop it when the sample components supported thereon reach the ion beam bombardment position and to move it at a high speed when the portion between the sample components passes through the ion bombardment position. The movement control program of the target 6 is shown in FIG. 5(A) and this control is made by a control signal from the computer 14 given to the target moving device 8.

Figure 5:
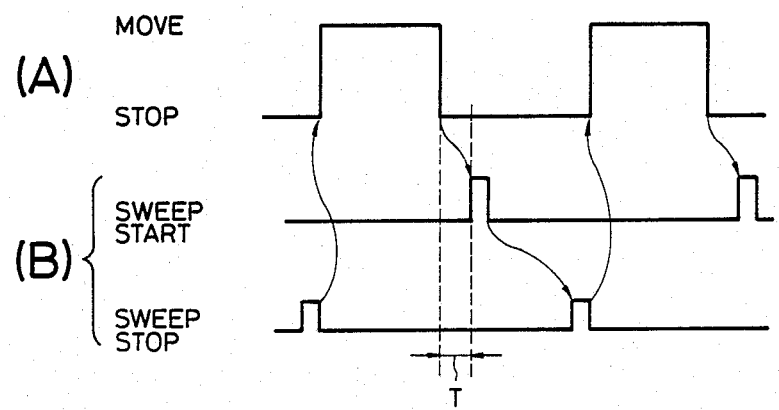
FIG. 5 is an explanatory view of target-and scan control.

Magnetic field sweeping from the magnetic field sweeping power source 16 is effected by the control signal from the computer 14 as shown in FIG. 5(B). In FIG. 5(B), symbol T represents a waiting time from the stop of the sample component at the ion bombardment position to the point of time when the quantity of secondary ions that are generated from the component portion gets stabilized. This waiting time can be set arbitrarily in advance by the computer 14 in accordance with the matrix such as glycerol.

Mass number sweeping, that is, scanning, is effected after the waiting time. This scanning is made in such a manner as to be finished before the start of movement of the target 6. Accordingly, the resulting spectrum is free from incorrectness and an accurate mass spectrum can be obtained.

The target control program such as shown in FIG. 5(A) can be prepared easily on the basis of the sample component position data that are stored in the computer 14 and are obtained by actual measurement.

Though the embodiment described above uses the ion beam as the primary beam, a fast speed atomic beam can be used in place of the ion beam. The atomic beam can be generated by, for example, neutralizing the ion beam 4 before it reaches the target 6.

It will be obvious to those skilled in the art that various changes and modifications can be made without departing from the scope and spirit of the present invention. Accordingly, the present invention is in no way limited to the embodiment given above.

What is claimed is:

1. A mass spectrometer comprising:
   means for generating a primary beam so that said primary beams is directed to a first predetermined position;
   means for holding a target carrying sample components;
   means for moving said target so that said sample components are situated at said first predetermined position;
   means for mass-dispersing ions that are generated by bombarding said sample components with said primary beam when said sample components are situated at said first predetermined position;
   means for effecting mass number sweeping so that the mass-dispersed ions having various mass numbers are passed through a second predetermined position;
   means for detecting the ions passing through said second predetermined position; and
   means for controlling said target moving means in such a manner as to stop said target when each of said sample components are situated at said first predetermined position and for controlling said mass number sweeping effecting means in such a manner so as to effect said mass number sweeping during the stoppage of said target and to start said mass number sweeping after the passage of a predetermined period from the stop of said target till the quantity of ions generated from said sample components are substantially stabilized.

2. A mass spectrometer according to claim 1, wherein said primary beam comprises an ion beam.

3. A mass spectrometer according to claim 1, wherein said target comprises a thin layer chromatography plate including a substrate and an adsorption layer formed on the surface of said substrate so as to carry said sample components.

4. A mass spectrometer according to claim 1, wherein said primary beam comprises an ion beam and said target includes a thin layer chromatography plate having a substrate and an adsorption layer formed on the surface of said substrate so as to carry said sample components.

5. A mass spectrometer comprising:
   means for generating a primary beam so that said primary beam is directed to a first predetermined position;
   means for holding a target carrying sample components;
   means for moving said target so that said sample components are situated at said first predetermined position;
   means for mass-dispersing ions that are generated by bombarding said sample components with said primary beam when said sample components are situated at said first predetermined position;
   means for effecting mass number sweeping so that the mass-dispersed ions having various mass numbers are passed through a second predetermined position;

means for detecting the ions passing through said second predetermined position; and means for controlling said target moving means in such a manner as to stop said target when each of said sample components are situated at said first predetermined position and for controlling said mass number sweeping effecting means in such a manner as to effect said mass number sweeping during stoppage of said target, to start said mass number sweeping after the passage of a predetermined period from the stop of said target till the quantity of ions generated from said sample components are substantially stabilized and to complete mass number sweeping before said target starts moving.

6. A mass spectrometer according to claim 5, wherein said primary beam comprises an ion beam.

7. A mass spectrometer according to claim 5, wherein said target comprises a thin layer chromatography plate including a substrate and an adsorption layer for supporting said sample components formed on the surface of said substrate.

8. A mass spectrometer according to claim 5, wherein said primary beam comprises an ion beam and said target includes a thin layer chromatography plate having a substrate and an adsorption layer for supporting said sample components formed on the surface of said substrate.

* * * * *